US009453830B2

(12) United States Patent
Zhang et al.

(10) Patent No.: US 9,453,830 B2
(45) Date of Patent: Sep. 27, 2016

(54) QUANTIFICATION OF ASPHALTENE INHIBITORS IN CRUDE OIL USING THERMAL ANALYSIS COUPLED WITH MASS SPECTROMETRY

(71) Applicant: Ecolab USA Inc., Eagan, MN (US)

(72) Inventors: Ying Zhang, Manvel, TX (US); Emerilis Casado-Rivera, Pearland, TX (US)

(73) Assignee: Ecolab USA Inc., St. Paul, MN (US)

( * ) Notice: Subject to any disclaimer, the term of this patent is extended or adjusted under 35 U.S.C. 154(b) by 209 days.

(21) Appl. No.: 14/473,287

(22) Filed: Aug. 29, 2014

(65) Prior Publication Data

US 2016/0061790 A1 Mar. 3, 2016

(51) Int. Cl.
*G01N 30/72* (2006.01)
*G01N 33/28* (2006.01)

(52) U.S. Cl.
CPC .......... *G01N 33/2835* (2013.01); *G01N 30/72* (2013.01); *G01N 33/28* (2013.01); *G01N 33/2823* (2013.01); *G01N 30/7206* (2013.01)

(58) Field of Classification Search
CPC .. G01N 30/72; G01N 30/7206; G01N 33/28; G01N 33/2823; G01N 33/2835
See application file for complete search history.

(56) References Cited

U.S. PATENT DOCUMENTS

| 5,394,733 | A | | 3/1995 | Acholla | |
|---|---|---|---|---|---|
| 6,051,535 | A | * | 4/2000 | Bilden | C09K 8/524 166/304 |
| 6,180,683 | B1 | * | 1/2001 | Miller | B01F 17/0092 8/39 |
| 2006/0116296 | A1 | * | 6/2006 | Kippie | C09K 8/12 507/244 |
| 2007/0221539 | A1 | * | 9/2007 | Cohrs | B01D 17/047 208/18 |
| 2008/0099207 | A1 | * | 5/2008 | Venditto | C09K 8/52 166/308.3 |
| 2014/0338915 | A1 | * | 11/2014 | Ferm | E21B 43/26 166/307 |
| 2015/0152329 | A1 | * | 6/2015 | Seetharaman | C09K 8/54 422/16 |

OTHER PUBLICATIONS

J. C. del Rio, et al. "Flash pyrolysis-gas chromatography of the kerogen and asphaltene fractions isolated from a sequence of oil shales" Journal of Chromatography A, 657 (1993) 119-22.*

C. Magnier and A. Y. Huc. "Pyrolysis of asphaltenes as a tool for reservoir geochemistry" Organic Geochemistry, vol. 23, No. 10, 963-967 (1995).*

Binkley, J., "Quantitative Characterization of Polymer Blends by Pyrolysis-Gas Chromatography-Time of Flight Mass Spectrometry (Pyr-GC-TOFMS)," Chromatography Online, LECO Corporation, Accessed from <http://license.icopyright.net/user/viewFreeUse.act?fuid=MTc5OTUyNjc%3D> on Apr. 1, 2014, 4 pages.

(Continued)

*Primary Examiner* — Peter Macchiarolo
*Assistant Examiner* — Natalie Huls
(74) *Attorney, Agent, or Firm* — Senniger Powers LLP

(57) ABSTRACT

The present invention generally relates to a novel method for the characterization and quantification of involatile macromolecules in hydrocarbon samples of crude oil. More particularly, the method utilizes pyrolysis/gas chromatography/mass spectrometry (PY/GC/MS, PY/GC/MS/MS or PY/GC/triple quad MS) to detect and quantify polymeric asphaltene inhibitors in crude oil.

21 Claims, 12 Drawing Sheets

(56) References Cited

OTHER PUBLICATIONS

Selsbo, P., et al., "Quantitative Analysis of Sulfur in Coal by Pyrolysis-Gas Chromatography and Multivariate Data Analysis," Energy & Fuels, 1996, pp. 751-756, vol. 10, No. 3.

Wang, F. C.-Y., et al., "Qualitative and Quantitative Analysis of A Thermoset Polymer, Poly(benzoxazine), by Pyrolysis-Gas Chromatography," Journal of Chromatography A, 2000, pp. 217-224, vol. 886.

* cited by examiner

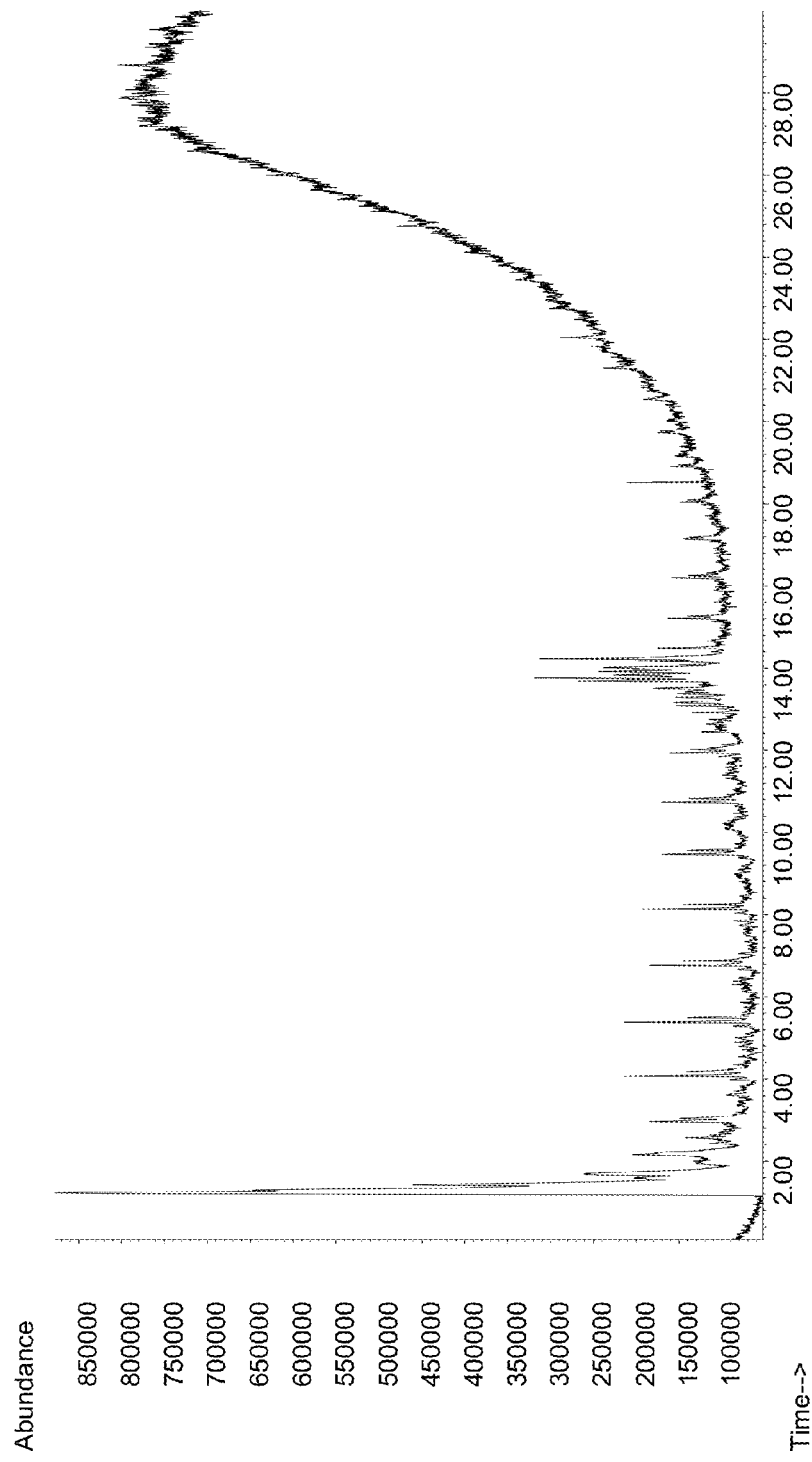

QUANTIFICATION OF ASPHALTENE INHIBITORS IN CRUDE OIL USING THERMAL ANALYSIS COUPLED WITH MASS SPECTROMETRY

FIELD OF THE INVENTION

The present invention generally relates to a method for the characterization and quantification of macromolecules in hydrocarbon samples of crude oil. More particularly, the method utilizes pyrolysis/gas chromatography/mass spectrometry (e.g., PY/GC/MS, PY/GC/MS/MS or PY/GC/triple quad MS) to detect and quantify polymeric asphaltene inhibitors in crude oil.

BACKGROUND OF THE INVENTION

Crude oils are comprised of two major solubility fractions, maltenes and asphaltenes. Maltenes constitute the fraction of oil that is soluble in low molecular mass n-alkane solvents, such as n-pentane, n-hexane, and n-heptane. Asphaltenes are defined as the crude oil fraction that is soluble in aromatic solvents and insoluble in low-boiling straight chain alkanes. Asphaltene molecules have complex structures and are typically polar molecules with relatively high molecular weights (approximately 700 to 1,000 g/mole). Asphaltenes can contain carbon, hydrogen, nitrogen, oxygen, and sulfur, as well as trace amounts of vanadium and nickel.

Asphaltenes are typically stable under virgin reservoir conditions, but can be destabilized and precipitate from crude oil during production due to changes in temperature, pressure, chemical composition, and shear rate. Asphaltene deposits can occur throughout the production system, from inside the reservoir formation to pumps, tubing, wellheads, safety valves, flow lines, and surface facilities used in the extraction process. Asphaltene deposits can cause production rate decline and other operational problems, such as increased fluid viscosity and density, and stabilization of oil-water emulsions. The nature of asphaltene deposits, which can appear hard and coal-like or sticky and tar-like, is determined by the composition of the crude oil and the conditions under which precipitation occurred.

Chemical treatment with additives such as dispersants and inhibitors is one of the commonly adopted control options for the remediation and prevention of asphaltene deposition. In general, asphaltene dispersants (ADs) are nonpolymeric surfactants. The polar and/or aromatic head groups in ADs are thought to interact with aggregated asphaltenes and make them more dispersible in the crude oil. Asphaltene inhibitors (AIs) are typically polymers. AIs provide real inhibition in that they can shift asphaltene flocculation pressure and prevent aggregation of asphaltene molecules. Determination of AI concentration in crude oil production is important for understanding the residence time of polymers down-hole as well as the effectiveness of precipitation reduction.

Techniques such as liquid chromatography-time of flight mass spectrometry (LC-TOF MS) have been used in the past to quantify residual asphaltene inhibitor in crude oil. However, the sample preparation procedure is very time consuming and expensive. In addition, LC-TOF MS may have limitations in use for different types of polymeric asphaltene inhibitors. Thus, an improved method for the detection and quantification of phenolic formaldehyde polymer type AIs in crude oil is still needed.

SUMMARY OF THE INVENTION

A method is provided for determining the content of an asphaltene inhibitor in a hydrocarbon sample. The method comprises: (i) pyrolyzing a known amount of a hydrocarbon sample to form fragments of the asphaltene inhibitor; (ii) separating the asphaltene inhibitor fragments using a gas chromatographic method; and (iii) detecting the asphaltene inhibitor fragments with a mass spectrometer.

Other objects and features will be in part apparent and in part pointed out hereinafter.

BRIEF DESCRIPTION OF THE DRAWINGS

FIG. 4A depicts the total ion chromatogram (TIC) obtained by on-line PY/GC/MS of treated oil sample of Example 4 and FIG. 4B depicts the corresponding extracted ion chromatogram (EIC) at m/z 135.

Corresponding reference characters indicate corresponding parts throughout the drawings.

DETAILED DESCRIPTION

Figure 1:
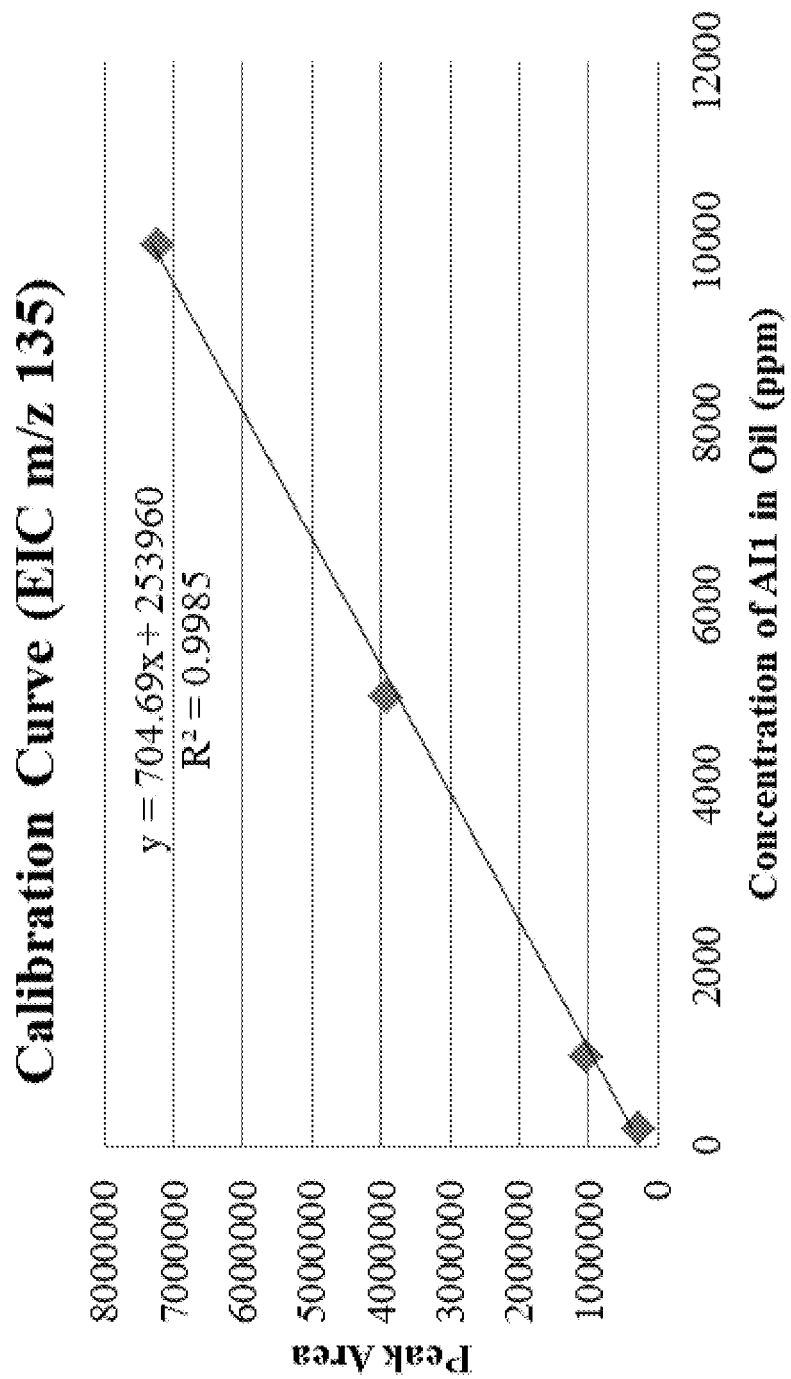
FIG. 1 depicts the standard calibration curve for asphaltene inhibitor (AI1) comprising a p-nonylphenol-formaldehyde polymer available from Nalco as Product No. EC6849A in untreated oil corresponding to the data in Example 4.
Figure 2A:
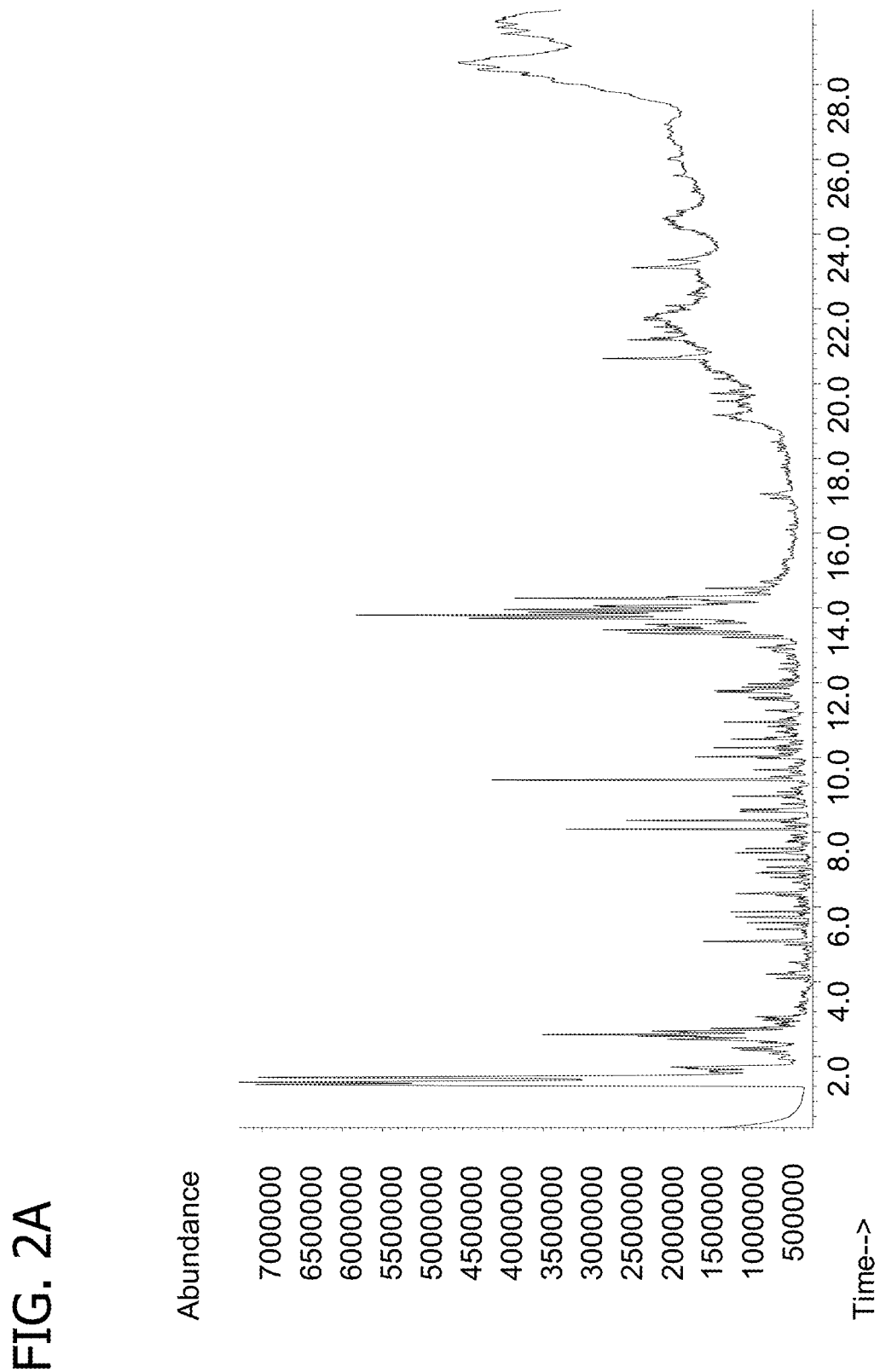
FIG. 2A depicts the total ion chromatogram (TIC) obtained by on-line PY/GC/MS of asphaltene inhibitor AI1 and FIG. 2B depicts the corresponding extracted ion chromatogram (EIC) at m/z 135.
Figure 2B:
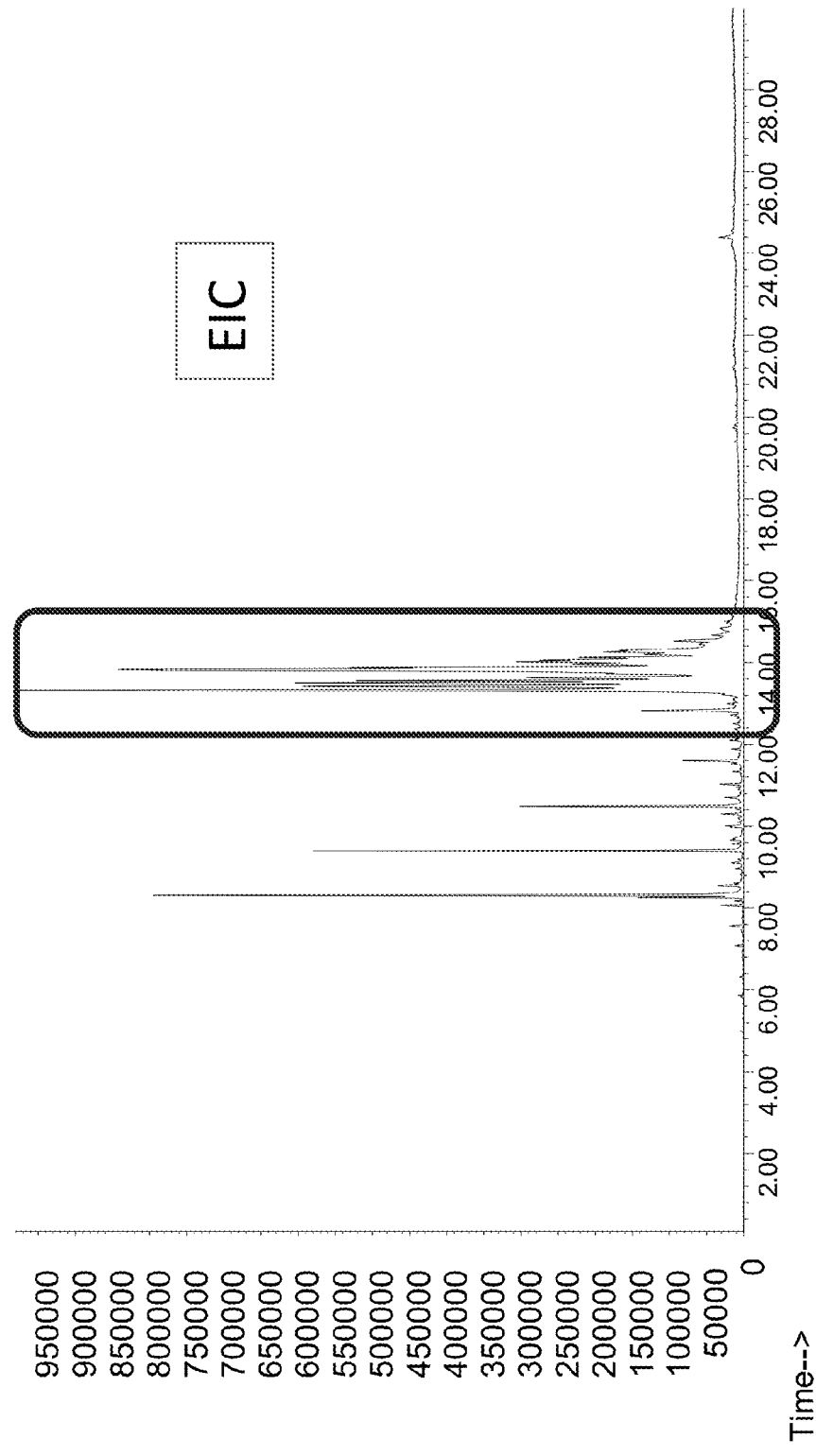
Figure 3A:
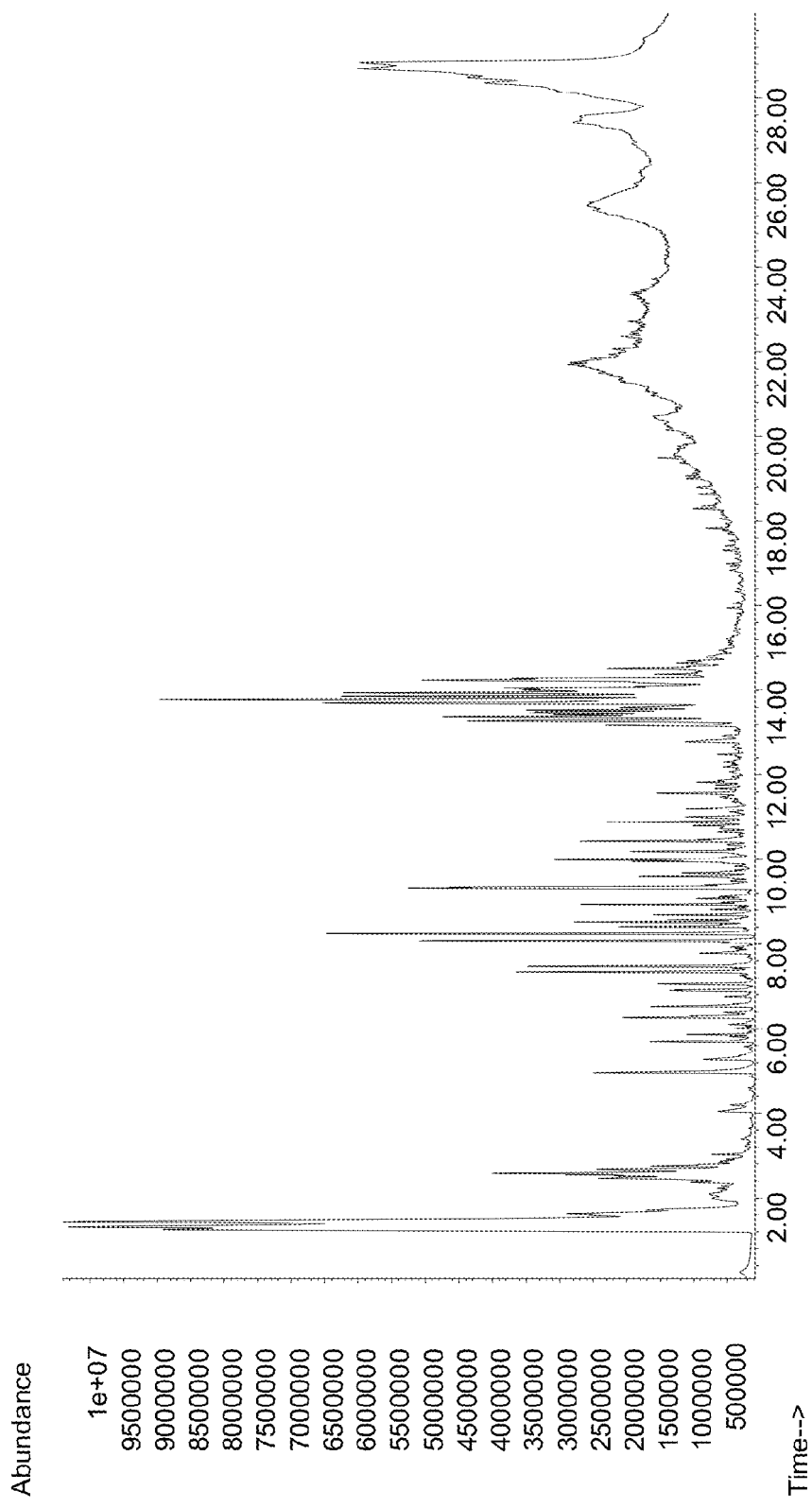
FIG. 3A depicts the total ion chromatogram (TIC) obtained by on-line PY/GC/MS of p-nonylphenol-formaldehyde polymer of Structure (I) and FIG. 3B depicts the corresponding extracted ion chromatogram (EIC) at m/z 135.
Figure 3B:
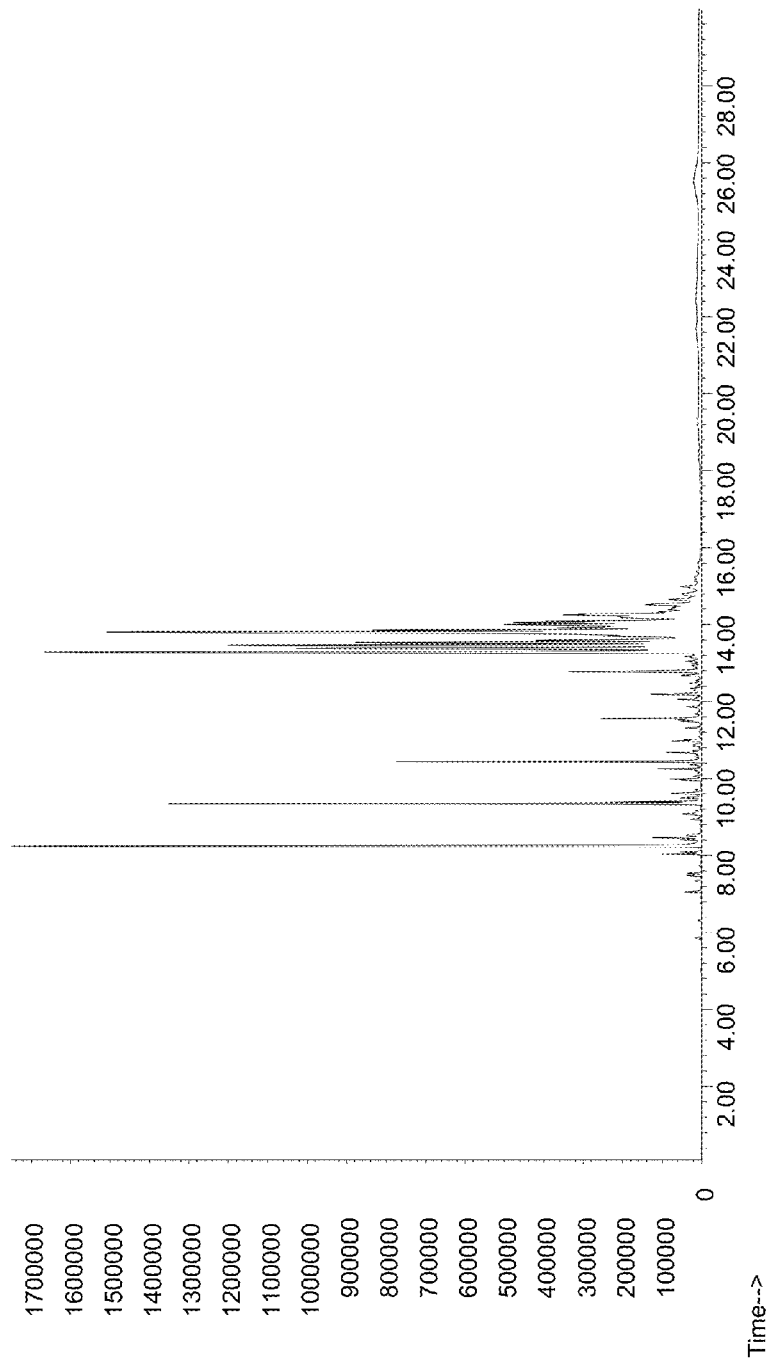
Figure 4B:
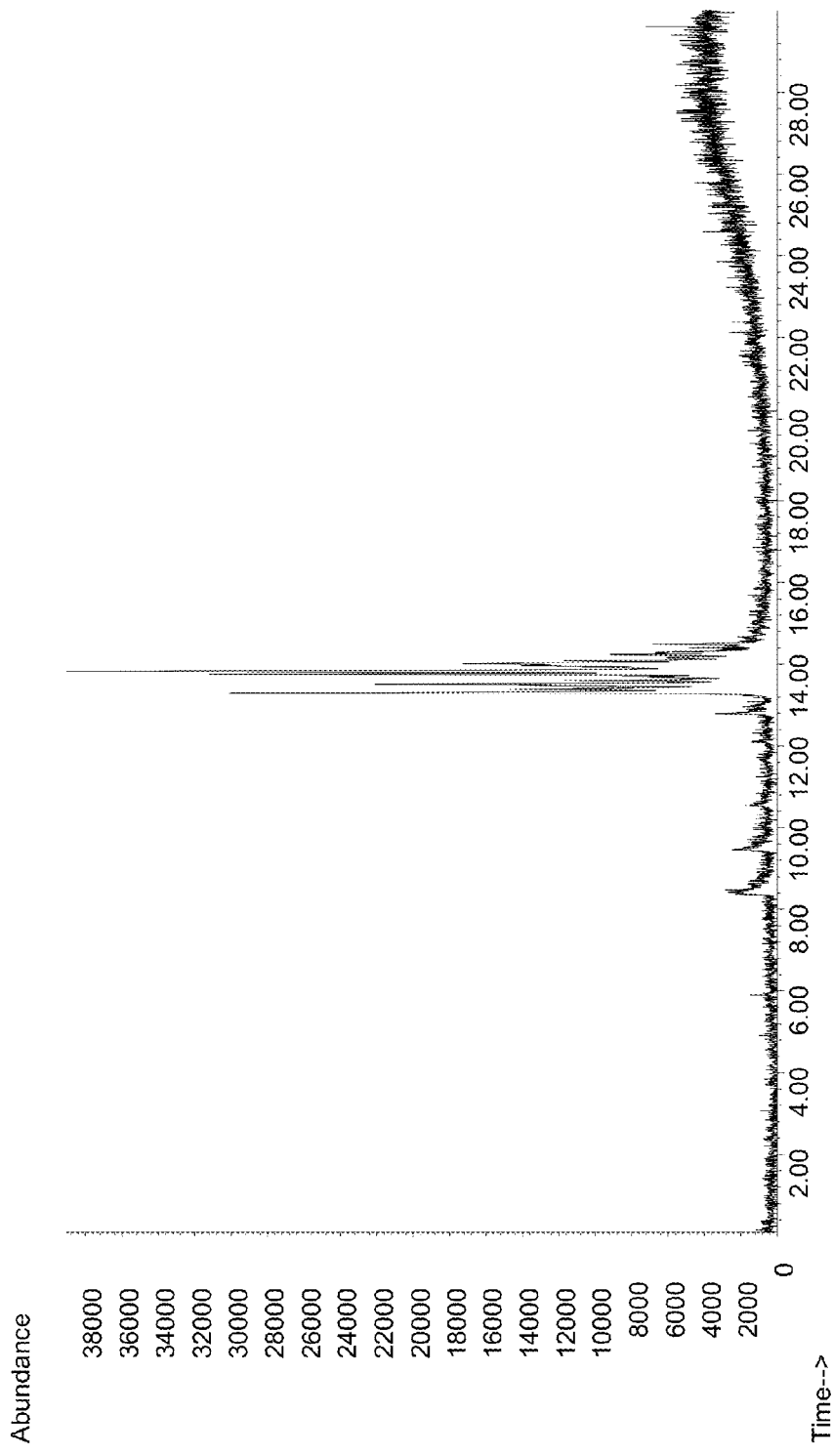
Figure 5A:
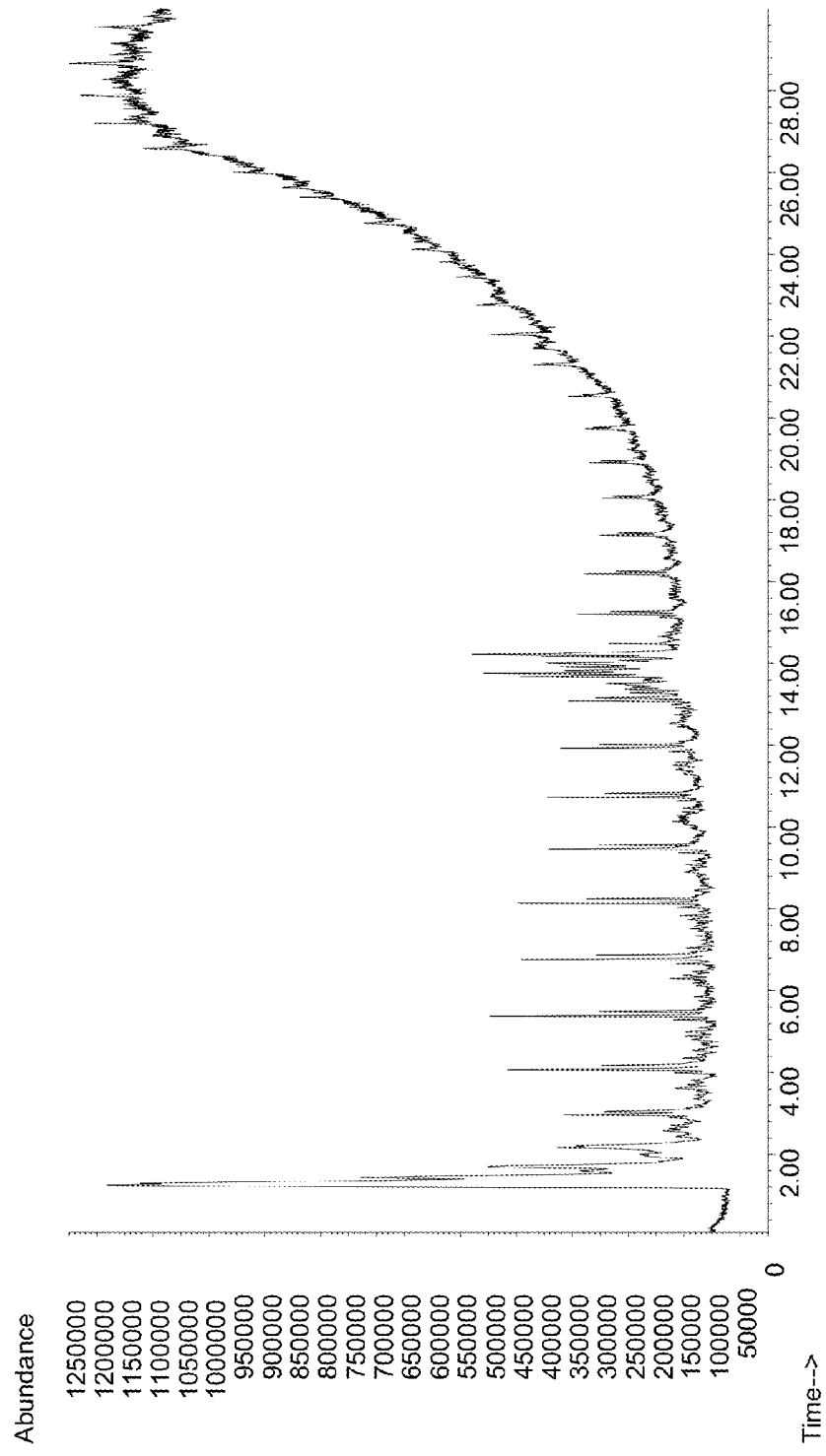
FIG. 5A depicts the total ion chromatogram (TIC) obtained by on-line PY/GC/MS of oil spiked with 10,000 ppm (v/v) AI1
Figure 5B:
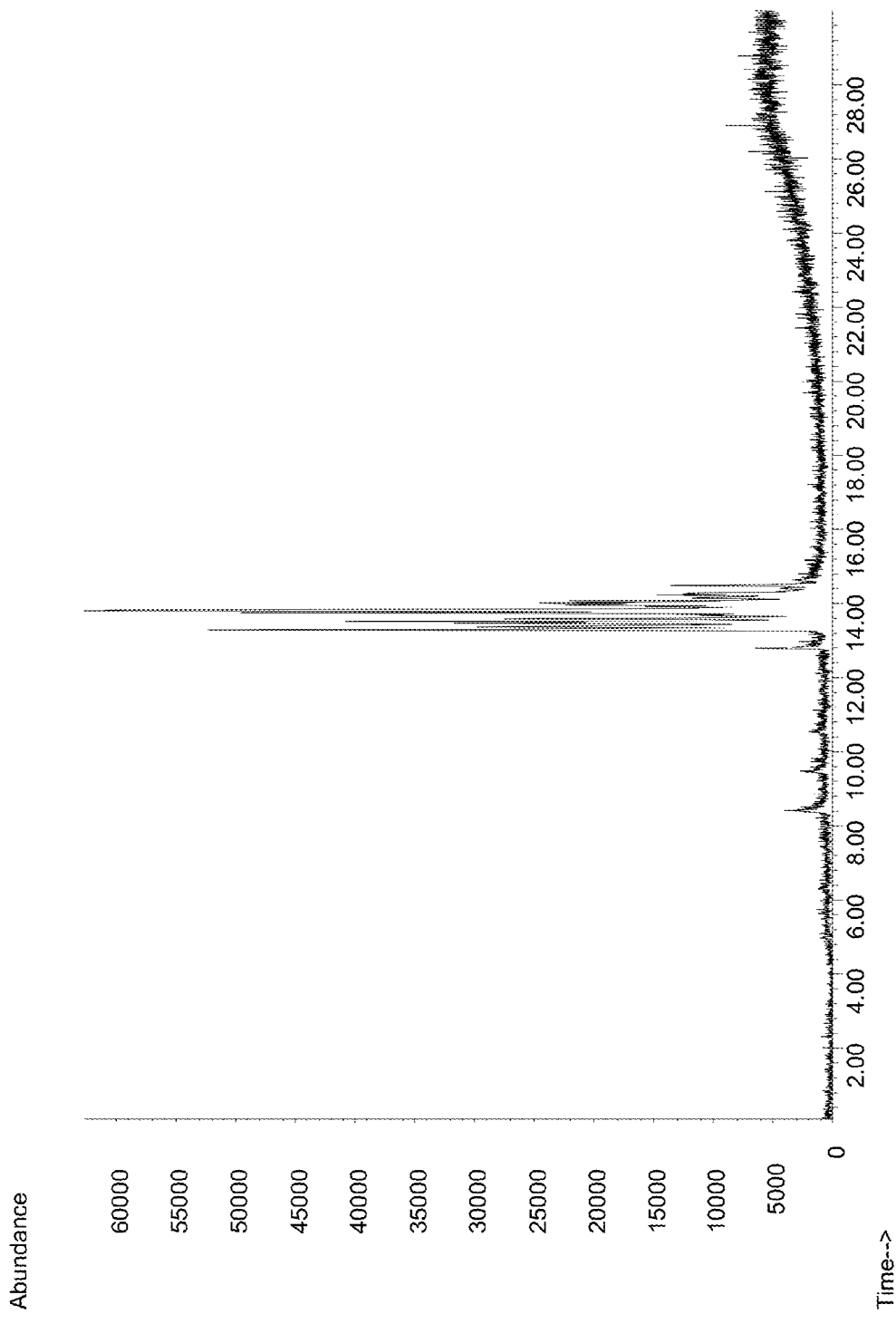
FIG. 5B depicts the corresponding extracted ion chromatogram (EIC) at m/z 135.
Figure 6A:
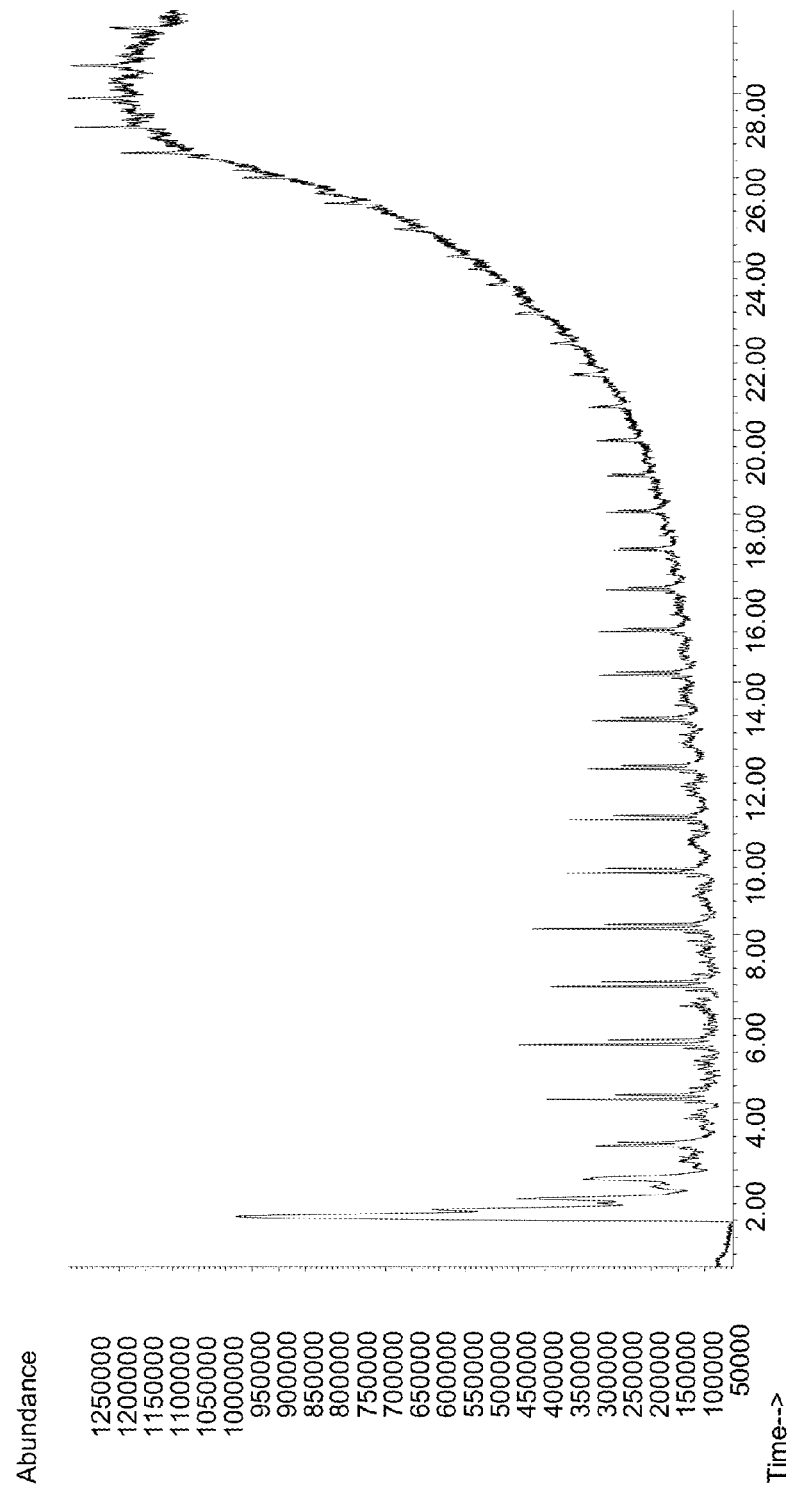
FIG. 6A depicts the total ion chromatogram (TIC) obtained by on-line PY/GC/MS of oil spiked with 200 ppm (v/v) AI1 and FIG. 6B depicts the corresponding extracted ion chromatogram (EIC) at m/z 135.
Figure 6B:
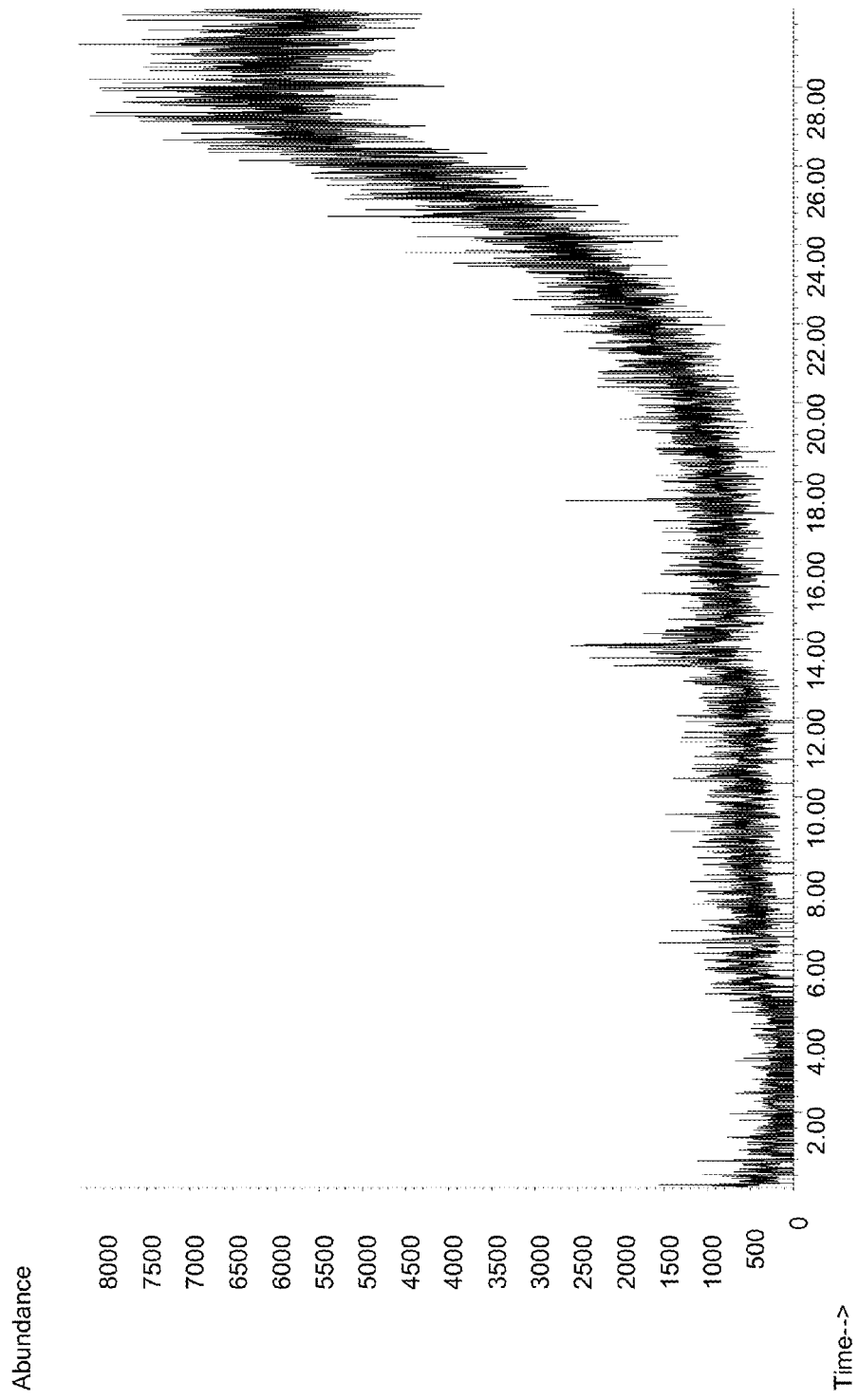
Figure 7:
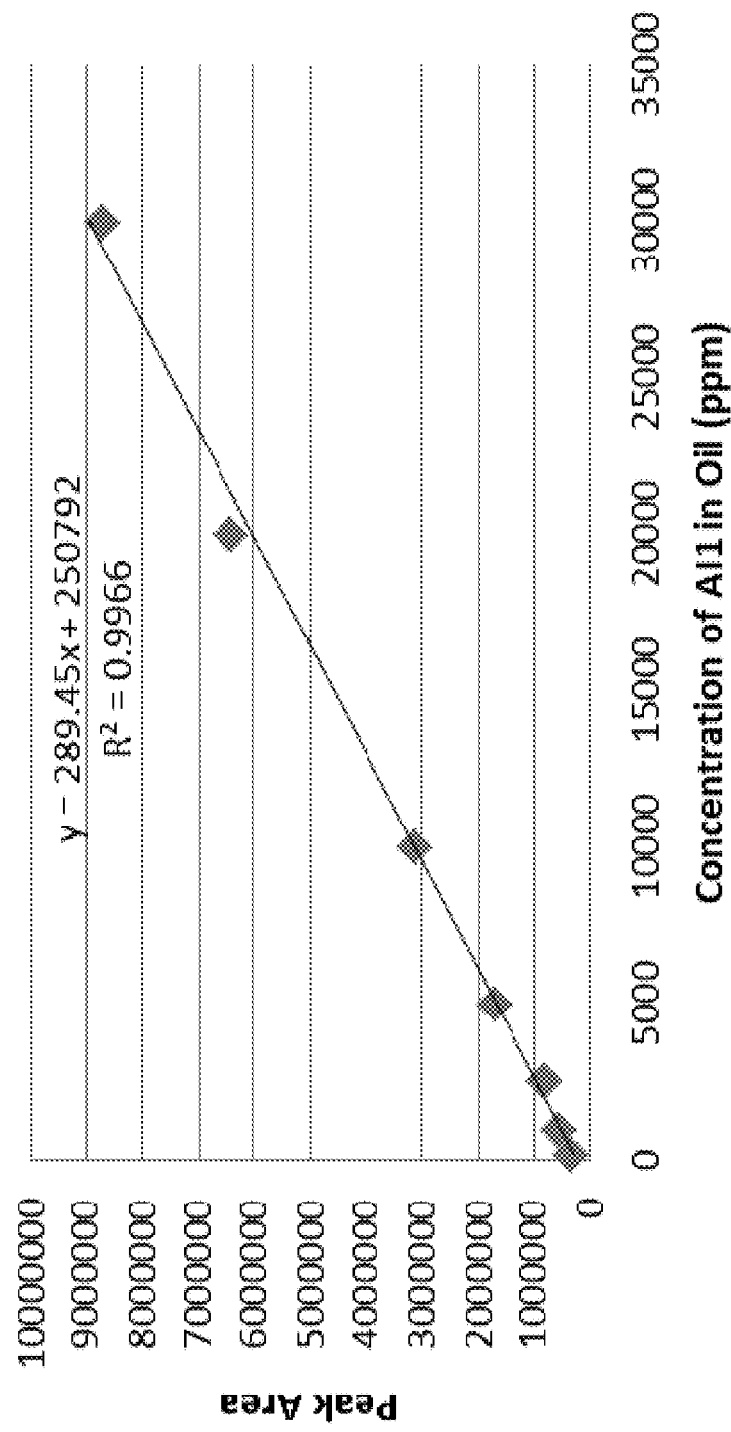
FIG. 7 depicts a second calibration curve for asphaltene inhibitor AI1 in untreated oil that corresponds to results in Example 5.

Polymers cannot be analyzed in their normal state by traditional gas chromatography (GC) because of their high molecular weight and lack of volatility. However, by heating these macromolecules to elevated temperatures (e.g., 500-1400° C.) they can be degraded into smaller compounds, which can be separated chromatographically and identified by mass spectrometry. Typically, the sample is inserted into a quartz chamber of a pyrolysis unit and heated resistively in an oxygen free environment at a pre-set temperature for a number of seconds. This results in a heat mediated cleavage of the chemical bonds within the macromolecule and produces lower molecular weight chemical moieties in the pyrolyzate. The compounds in the pyrolyzate are then swept onto the column of the gas chromatograph, separated according to their interactions with the stationary phase, and detected by a mass spectrometric (MS) detector. Pyrolysis/gas chromatography/mass spectrometry (PY/GC/MS) allows for analysis of nonvolatile, difficult to separate macromolecules with minimal sample preparation.

PY/GC/MS is a destructive analytical technique. Most of the thermal degradation results from free radical reactions initiated by bond breaking and depends on the relative strengths of the bonds that hold the molecules together. If the energy transfer is controlled by temperature, heating rate, and heating time, the degradation pattern is reproducible and characteristic for the original polymer. In other words, another sample of the same composition heated at the same rate to the same temperature for the same period of time will produce the same decomposition products. The pyrolysis apparatus should provide rapid temperature rise, accurate temperature control, and a reproducible final pyrolysis temperature.

The instant invention provides a method for detecting and quantifying the amount of an asphaltene inhibitor in a hydrocarbon sample. The hydrocarbon sample can be a crude oil.

The asphaltene inhibitor that the method can be used to detect can be a polymer. Preferably, the asphaltene inhibitor comprises a phenol-formaldehyde polymer. An exemplary asphaltene inhibitor is AI1, commercially available from Nalco Champion. The major component of the asphaltene inhibitor is a p-nonylphenol-formaldehyde polymer having structure (I):

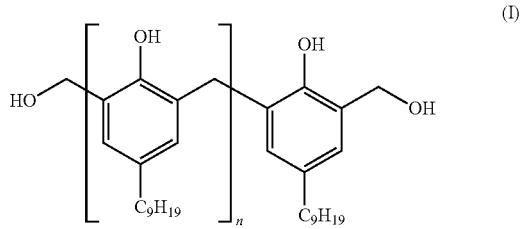

wherein n is an integer greater than 2.

The degradation products produced by pyrolysis of a polymer are volatile enough to be compatible with analysis by gas chromatography. In particular, the polymers having the structure of formula (I) can be pyrolyzed at high temperature. Separation of the degradation products in the pyrolyzate can be achieved using a capillary GC column. When coupled to a mass spectrometer, the stream of separated degradation products exits the GC column and enters the ionization chamber of the MS. The end of the GC column is placed into a GC/MS interface that allows the column to be heated during the transfer of the separated compounds from the GC to the ionization chamber of the MS. The degradation products are then bombarded with electrons (e.g., 70 eV), resulting in ion formation and subsequent fragmentation. Electron impact ionization (EI), for example, results in removal of one electron to give a molecular cation ($M^+$) having the same nominal mass as the neutral compound. The resulting positive ions are directed into a mass analyzer (quadrupole) where they are separated based on their mass-to-charge ratio (m/z). Only a narrow range of ions having a specified m/z ratio are allowed to pass at any given time. From here, the ions enter the mass detector (electron multiplier) and are recorded by the controlling computer, which knows which m/z is exiting the mass analyzer at that instant.

When operated in Full Scan mode, the quadrupole continuously and repeatedly ramps the monitored m/z ratio from a preset lower limit to a preset upper limit, and will detect all ions within that m/z range over a set period of time. A typical mass scan range will cover 35-500 m/z four times per second. At the conclusion of each individual scan, the intensities of all m/z ratios within that scan are summed, giving a total ion current. The total ion current (TIC) chromatogram is a summation of all the m/z intensities for each individual mass spectrum (y-axis) plotted as a function of time (x-axis).

Alternatively, the data obtained by GC/MS can be displayed in three dimensions, like a cube, to make use of the fact that repetitive scan GC/MS data are really a three-dimensional matrix of data (x=time, y=total ion current, and z=m/z). Further, one can choose to plot a single m/z signal vs. time. This Extracted Ion Chromatogram (EIC) allows the mass spectrometer to be used as a selective detector.

The PY/GC/MS of asphaltene inhibitor AI1 p-nonylphenol-formaldehyde polymer of Structure (I) at a pyrolysis temperature ranging from 500 to 600° C. for 5 to 10 seconds generates a characteristic fragment at m/z 135 (e.g., possibly a phenol substituted with a propyl group). Thus, this fragment can be used as an indicator for quantifying AI1 in crude oil samples.

In order to quantify the amount of AI1 in production samples of crude oil, a calibration curve was prepared using untreated samples of oil spiked with known concentrations of the AI. A calibration curve shows the relationship between the response of the analytical instrument and a known amount of an analyte introduced into the instrument. The calibration curve was analyzed using a linear least squares regression. More specifically, a first-order least squares regression model of the form y=mx=b, (where y=detector response and x=target compound amount or concentration) was used using a minimum of at least three external standards of varying concentration.

As shown in FIG. 1, the calibration curve had good linearity ($R2=0.0085$), and the limit of detection was 200 ppm (v/v). In other words, the lowest concentration of AI1 in the oil sample must be greater than about 200 ppm to give a detectable signal using the method described herein.

As generally known in the art, a squeeze process can be used to deliver the asphaltene inhibitor to a deepwater well. The first step involves cleaning out and flowing back the well, then pumping in activator and an oil spacer. In the second step, the AI agent is injected. The third step comprises a post-flush with crude oil. In the fourth and final step, the well is shut in for 12 to 24 hour, giving the activator and inhibitor time to form a complex before production begins. This method increases the residence time for AI in the formation (possibly cite "Asphaltenes-Problematic but Rich in Potential").

Alternatively, the asphaltene inhibitor can be applied to a deepwater well using a continuous injection process. This process uses a capillary or umbilical line to deliver the asphaltene inhibitor continuously to the deepwater well contents.

For both the squeeze and continuous injection processes, the sample for testing using the analytical method of the invention is usually collected at the top of the well.

Generally, the pyrolysis step can be conducted at a temperature of from about 500° C. to about 800° C., preferably at a temperature of from about 550° C. to about 700° C., and more preferably at a temperature from about 550° C. to about 600° C. For purposes of this specification, pyrolysis temperature refers to temperature of the device providing heat to the sample (e.g., pyrolyzer furnace temperature), not the temperature of the sample.

Generally, the pyrolysis step can be conducted for a time interval ranging from about 3 to about 10 seconds, preferably from about 5 to about 7 seconds, and more preferably about 6 seconds. For purposes of this specification, pyrolysis time refers to time that the sample is subjected to the pyrolysis temperature.

The amount of hydrocarbon sample that is pyrolyzed according to the method described herein can be at least 0.5 mg, at least 0.7 mg, or at least 0.9 mg. Generally, the amount of hydrocarbon sample that is pyrolyzed can range from about 0.5 to about 3 mg, preferably from about 0.7 to about 2.5 mg, and more preferably from about 1 to about 2 mg.

Preferably, about 1 to about 2 mg of the hydrocarbon sample is pyrolyzed at a temperature of about 550° C. for about 6 seconds.

A suitable pyrolysis apparatus for pyrolysis of the hydrocarbon sample prior to analysis by GC/MS can be done with a pyrolysis unit linked to a gas chromatograph, such as a Double-shot Pyrolyzer PY-2020iD (Frontier Laboratories LTD, Fukushima, Japan).

Separation of the degradation products can be carried out between a stationary phase and a gas mobile phase. As those skilled in the art will appreciate, this separation can be accomplished by using gas chromatography, which may also be referred to as gas-liquid partition chromatography (GLPC), which may also be referred to simply as gas chromatography (GC). The GC techniques can be practiced, for example, using a J&W DB-5ms Ultra Inert (UI) 30 m×0.25 mm×0.25 µm capillary column (Agilent Technologies, Inc.; Santa Clara, Calif.), having a stationary phase comprising 5% phenyl –95% dimethyl polysiloxane groups.

The temperature profile within the gas chromatography column can begin with an initial temperature of from about 50° C. to about 75° C., preferably from about 55° C. to about 70° C., and more preferably from about 55° C. to about 65° C. The temperature profile can include maintaining this initial temperature for a period from about 0 to about 4 minutes, from about 0 to about 3 minutes, or from about 0 to about 1 minute.

The temperature within the GC column can be increased at a rate of from about 5° C. to about 20° C. per minute, at a rate of from about 8° C. to about 15° C. per minute, or at a rate of from about 9° C. to about 11° C. per minute. The temperature profile may end with a final temperature of from about 300° C. to about 350° C., from about 310° C. to about 340° C., or from about 320° C. to about 330° C.

In GC analysis utilizing a thirty meter column, the flow rate through the column can be at least 0.5 mL/minute, at least 1.0 mL/minute, or at least 1.3 mL/minute. The flow rate can range may be from about 0.5 mL/minute to about 5 mL/minute, from about 0.5 mL/minute to about 3 mL/minute, from about 0.5 mL/minute to about 1.5 mL/minute or from about 1 mL/minute to about 1.5 mL/minute.

Having described the invention in detail, it will be apparent that modifications and variations are possible without departing from the scope of the invention defined in the appended claims.

EXAMPLES

The following non-limiting examples are provided to further illustrate the present invention.

Example 1

Instrumentation for PY/GC/MS Analysis of Asphaltene Inhibitor AI1 in Crude Oil Samples A Double-shot Pyrolyzer PY-2020iD (Frontier Laboratories LTD, Fukushima, Japan) was used for the pyrolysis step. A stainless steel disposable eco-cup was charged with 1-2 mg of crude oil sample, and the sample weight was recorded. A total of 27 production samples of crude oil (e.g., the crude oil were from Mississippi land-based oil wells containing residual AI1 were used as is (e.g., no additional treatments were performed before analysis).

Volatile components within the crude oil sample were desorbed at a programmed rate of 80° C. to 300° C. at 30°/min (1 minute hold). This was followed instantly by pyrolysis of the residual sample at 550° C. for 0.1 minutes.

The pyrolyzer unit was directly connected to the injector port of a 7890A Gas Chromatograph (Agilent Technologies Inc., Santa Clara, Calif.) with a series 5973C quadrupole mass spectrometer (Agilent Technologies Inc., Santa Clara, Calif.) operated in electron impact ionization (EI) mode. The pyrolyzate was then introduced into the GC capillary column using a metal needle that directly connected the pyrolysis oven to the GC capillary column.

The gas chromatograph was equipped with an Agilent J&W DB-5ms Ultra Inert (UI) polysiloxane capillary column (30 m length×0.25 mm I.D.×0.25 µm stationary phase film thickness). Helium was used as the carrier gas. The helium flow rate was 1 mL/minute. The gas chromatograph had a temperature program using an initial temperature of 60° C. and a final temperature of 325° C. at a heating rate of 10° C./minute and a hold time at 325° C. of 3.5 minutes for a total time of 30 minutes.

The temperature of the GC inlet was 300° C. and the split ratio was 200:1. Mass spectra and reconstructed chromatograms (total ion current [TIC]) were obtained by automatic scanning in the mass range m/z 10 to 550 m/z (i.e., full scan detection). GC/MS data were processed with Agilent ChemStation software and the Wiley NIST11 mass spectra library.

Example 2

Preparation of a Calibration Curve for the Quantification of Asphaltene Inhibitor AI1

The asphaltene inhibitor analyzed was AIL available from Nalco Champion as Product No. EC6849A. The major component of the asphaltene inhibitor is a p-nonylphenol-formaldehyde polymer. For the calibration curve of FIG. 1, calibration standards were prepared by dissolved AI1 in untreated oil at 10,000 ppm. A series of standards solutions were made by diluting the stock solution to 5,000 ppm, 1,000 ppm, 200 ppm, and 100 ppm (v/v) with untreated oil. Untreated oil was used as the solvent to prepare the calibration standard solutions in order to compensate for the matrix effect of the complex crude oil. If a solvent other than untreated oil would have been used, the percent recovery in each solvent would have required consideration.

Calibration points were collected for untreated crude oil spiked with AI chemical AI1 at five concentrations ranging from 100 to 10,000 ppm. As shown in FIG. 1, the calibration curve has good linearity (R2=0.9985). The limit of detection was 200 ppm (v/v).

Example 3

Quantification of AI1 Residual in Samples of Crude Oil

A batch of ten crude oil samples was analyzed according to the method in order to determine the concentration of asphaltene inhibitor AI1 Samples of crude oil were collected at progressive time intervals after an inhibitor squeeze over a four day period. The oil samples were collected at the top of the well at the prescribed time. The results are shown in Table 1. This analysis shows that the method used can detect and quantify AI1 present in crude oil without extensive sample preparation or long analysis times.

TABLE 1

Concentrations of AI1 residual in oil samples

| Sample No. | Time (h) | Concentration of AI1 (ppm, v/v) |
|---|---|---|
| untreated |  | <200 |
| 1 | 0 | 5901 |
| 2 | 1 | 8349 |
| 3 | 2 | 9111 |
| 4 | 3 | 6421 |
| 5 | 14.5 | 681 |
| 6 | 23 | <200 |
| 7 | 38 | <200 |
| 8 | 47 | <200 |
| 9 | 62 | <200 |
| 10 | 71 | <200 |

Example 4

Quantification of AI1 Residual in Samples of Crude Oil

Similar to the method of example 3, for the calibration curve of FIG. 1, calibration standards were prepared by dissolved AI1 in untreated oil at 30,000 ppm. A series of standards solutions were made by diluting the stock solution to 20,000 ppm, 10,000 ppm, 5,000 ppm, 1,000 ppm, 200 ppm, and 100 ppm (v/v) with untreated oil. Untreated oil was used as the solvent to prepare the calibration standard solutions in order to compensate for the matrix effect of the complex crude oil.

| Sample | concentration (ppm, v/v) |
|---|---|
| untreated | <200 |
| 0 h | 10979 |
| 1 h | 32453 |
| 2 h | 26108 |
| 3 h | 19995 |
| 4 h | 17876 |
| 5 h | 18418 |
| 6 h | 18100 |
| 7 h | 13211 |
| 8 h | 17997 |
| 9 h | 17306 |
| 10 h | 13678 |
| 11 h | 8312 (low) |
| 12 h | 14934 |
| 26 h | 4074 |
| 31 h | 1594 |
| 49 h | 1352 |
| 56.5 h | 1550 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the methods without departing from the scope of the invention, it is intended that all matter contained in the above description and shown in the accompanying drawings shall be interpreted as illustrative and not in a limiting sense.

What is claimed is:

1. A method for determining the content of an asphaltene inhibitor in a hydrocarbon sample, the method comprising:
   pyrolyzing a known amount of a hydrocarbon sample to form a degradation product of the asphaltene inhibitor;
   separating the asphaltene inhibitor degradation product using a gas chromatographic method; and
   detecting the asphaltene inhibitor degradation product with a mass spectrometer.

2. The method of claim 1 wherein the hydrocarbon sample is a crude oil.

3. The method of claim 2 wherein the asphaltene inhibitor is a polymer.

4. The method of claim 2 wherein the hydrocarbon sample is pyrolyzed at temperatures ranging from about 500° C. to about 800° C.

5. The method of claim 4 wherein the hydrocarbon sample is pyrolyzed at temperatures ranging from about 550° C. to about 700° C.

6. The method of claim 5 wherein the hydrocarbon sample is pyrolyzed at temperatures ranging from about 550° C. to about 600° C.

7. The method of claim 2 wherein the hydrocarbon sample is pyrolyzed for about 3 to about 10 seconds.

8. The method of claim 7 wherein the hydrocarbon sample is pyrolyzed for about 5 to about 7 seconds.

9. The method of claim 8 wherein the hydrocarbon sample is pyrolyzed for about 6 seconds.

10. The method of claim 2 wherein the hydrocarbon sample is heated at a temperature from about 80° C. to about 325° C. at a rate from about 20° C. to about 40° C. per minute.

11. The method of claim 10 wherein the hydrocarbon sample is heated at a temperature from about 80° C. to about 300° C. at a rate of about 30° C. per minute.

12. The method of claim 10 wherein the hydrocarbon sample is held at a temperature from about 300° C. to about 325° C. for about 30 seconds to 90 seconds.

13. The method of claim 12 wherein the hydrocarbon sample is held at a temperature at about 300° C. for about 60 seconds.

14. The method of claim 2 wherein the mass spectrometer detects a single mass/charge ratio value.

15. The method of claim 2 wherein the mass spectrometer detects a range of mass/charge ratio values.

16. The method of claim 2 wherein the asphaltene inhibitor is a polymer.

17. The method of claim 2 wherein the asphaltene inhibitor degradation products are ionized.

18. The method of claim 17 wherein the asphaltene inhibitor degradation products are quantitatively detected by mass spectrometry.

19. The method of claim 18 wherein the quantitative detection by mass spectrometry comprises comparing the peak area of a single mass/charge ratio associated with an asphaltene inhibitor fragment with a range of peak areas for the same single mass/charge ratio measured for an external calibration curve.

20. The method of claim 19 wherein the external calibration curve is determined by measuring the peak area of a single mass/charge ratio associated with the asphaltene inhibitor fragment for at least three samples containing a range of known concentrations of the asphaltene inhibitor in the hydrocarbon fluid and plotting the peak area of the single mass/charge ratio against the known concentration of the asphaltene inhibitor.

21. The method of claim 2 wherein the gas chromatographic method uses a polysiloxane capillary column.

* * * * *